(12) United States Patent
Friesem et al.

(10) Patent No.: US 6,228,022 B1
(45) Date of Patent: *May 8, 2001

(54) METHODS AND INSTRUMENTS FOR SPINAL SURGERY

(75) Inventors: Tai Friesem, Kfar Saba (IL); Mingyan Liu, Bour-la-Reine; Loic Josse, Palaja, both of (FR)

(73) Assignee: SDGI Holdings, Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/181,153

(22) Filed: Oct. 28, 1998

(51) Int. Cl.⁷ .................................................. A61B 17/02
(52) U.S. Cl. ..................... 600/204; 600/207; 600/153; 604/164; 606/185; 606/198
(58) Field of Search ..................... 600/204, 104, 600/108, 115, 116, 153, 207; 604/102, 164, 105, 106, 107, 108, 109; 606/192, 198, 185, 179

(56) References Cited

U.S. PATENT DOCUMENTS

| 3,750,667 | * | 8/1973 | Pshenichny et al. | 604/164 |
| 4,545,374 | * | 10/1985 | Jacobson | 604/164 |
| 5,158,543 | | 10/1992 | Lazarus | 604/164 |
| 5,195,541 | | 3/1993 | Obenchain | 128/898 |
| 5,273,026 | * | 12/1993 | Wilk | 606/198 |

(List continued on next page.)

FOREIGN PATENT DOCUMENTS

| 43 28 690 A1 | 2/1995 | (DE) . |
| WO93/14801 | 8/1993 | (WO) . |
| WO 94/17759 | 8/1994 | (WO) . |
| WO 97/23174 | 7/1997 | (WO) . |
| WO97/30666 | 8/1997 | (WO) . |
| WO98/04202 | 2/1998 | (WO) . |

OTHER PUBLICATIONS

*Laparoscopic Bone Dowel Surgical Technique,* Sofamor Danek The Spine Specialist, 1995.

*Surgical Technique Using Bone Dowel Instrumentation for Anterior Approach,* Sofamor Danek The Spine Specialist, 1996.

Primary Examiner—Gene Mancene
Assistant Examiner—Pedro Philogene
(74) Attorney, Agent, or Firm—Woodard, Emhardt, Naughton, Moriarty & McNett (57) ABSTRACT

Surgical techniques and instruments are provided for preparing a disc space for implantation of a vertebral fusion device or implant. In accordance with one embodiment of the technique, a surgical instrument assembly is provided having an outer sleeve with distraction fingers at one end to maintain distraction of a disc space. A switching sleeve having a pair of rotatable distractors is coupled within the outer sleeve, and the sleeves are placed over a dilator until the distractor heads are placed within the disc space. The dilator is withdrawn and the disc space distracted by rotating the distractors of the switching sleeve. The switching sleeve is uncoupled from the outer sleeve and the fingers of the outer sleeve are then inserted into the disc space. The switching sleeve and dilator are then removed and the outer sleeve defines a channel therethrough that allows insertion of implants at bilateral locations within the disc space without movement or manipulation of the outer sleeve. Laparoscopic procedures may be performed in the disc space by placing a sealing member over the end of the outer sleeve after it is inserted into the disc space.

29 Claims, 9 Drawing Sheets

U.S. PATENT DOCUMENTS

| | | | |
|---|---|---|---|
| 5,306,239 | * 4/1994 | Gurmarnik et al. | 604/164 |
| 5,334,150 | * 8/1994 | Kaali | 604/164 |
| 5,376,076 | * 12/1994 | Kaali | 604/164 |
| 5,484,437 | * 1/1996 | Michelson | 606/61 |
| 5,534,009 | 7/1996 | Lander | 606/185 |
| 5,551,947 | 9/1996 | Kaali | 604/264 |
| 5,569,205 | 10/1996 | Hart et al. | 604/167 |
| 5,569,290 | * 10/1996 | McAfee | 606/185 |
| 5,797,909 | * 8/1998 | Michelson | 606/61 |
| 6,004,326 | * 12/1999 | Castro et al. | 606/99 |

* cited by examiner

METHODS AND INSTRUMENTS FOR SPINAL SURGERY

BACKGROUND OF THE INVENTION

The present invention relates generally to methods and instruments for performing spinal surgery. Specifically, the invention concerns laparoscopic techniques and instruments to prepare a disc space for a vertebral implant.

The use of surgical techniques to correct the causes of low back pain, such as spinal injuries and deformities, has steadily increased over the last several years. One common procedure for relieving pain from the above-described problems is a discectomy, or surgical removal of a portion or all of an intervertebral disc, followed by implantation of a device between the adjacent vertebrae, such as a vertebral implant or fusion device. Typically, implantation of such a device is intended to promote bony fusion between the adjacent vertebral bodies.

Various surgical methods have been devised for implantation of devices into a subject disc space. For example, PCT International Publication No. WO 97/30666 to Zdeblick et al. discloses laparoscopic surgical techniques and instruments for preparing a disc space for implantation of fusion devices or implants. The laparoscopic instrumentation provides a sealed working channel to the disc space through which the disc space is distracted, the vertebral endplates and surrounding discs are reamed, and the vertebral implant inserted, all under direct vision through a laparoscopic port engaged to the end of the sleeve. In this technique, a single sleeve is alternately placed at bilateral locations on the disc space through a single incision in the skin for insertion of a pair of fusion devices or vertebral implants at each location. A switching sleeve extends through the outer sleeve of the laparoscope to protect the tissue at the surgical site as the outer sleeve of the laparoscope is moved between bilateral locations. In order to move the outer sleeve, the switching sleeve is inserted and then the distractor fingers of the outer sleeve are withdrawn from the disc space at the first bilateral location. The outer sleeve and the switching sleeve are then manipulated through the skin to the second bilateral location. The techniques and instruments of the '666 publication suffer from the disadvantage of requiring multiple manipulations of vessels and tissue adjacent the vertebral bodies to perform the procedure. Multiple manipulation of the vessels and tissues may increase the overall time of the procedure and increase the risk of damage to the vessels.

While the above described technique represents a significant advance over prior surgical procedures for preparation and insertion of a fusion devices or other implants in the disc space, a need for improvement remains. In particular, procedures and instruments are required that minimize trauma to tissue surrounding the surgical site while allowing bilateral implantation of fusion devices in the disc space. The present invention is directed to these needs, among others, in the field.

SUMMARY OF THE INVENTION

An apparatus for distracting a disc space is provided in accordance with one aspect of the invention. The apparatus includes a switching sleeve having a first end and an opposite second end. The sleeve defines a pair of distractor channels and a locking channel between said pair of distractor channels extending between the first and second ends. Preferably, a pair of distractors are rotatably received within a corresponding one of the distractor channels. Each of the distractors have a head extending from the first end, an engagement portion proximate the second end, and a stem extending between the head and the engagement portion. The locking channel is configured to receive a locking mechanism to lock the heads in an insertion position for insertion into the dilated disc space. The locking mechanism is movable after the heads are inserted into the disc space to release the heads for rotation to a second position to distract the disc space. Preferably, an outer sleeve is disposed about the switching sleeve and is selectively locked thereto.

In accordance with another aspect of the invention, an apparatus for use in preparing a disc space for insertion of a vertebral implant is provided. The apparatus includes an outer sleeve with a first end having a pair of opposite fingers extending therefrom and an opposite second end having a coupling mechanism. The outer sleeve defines a passage extending between the first end and the second end. A switching sleeve is removably disposed within the passage. Preferably, the switching sleeve has a pair of distractors at a first end. More preferably, each of the distractors is rotatable from an insertion position to a distraction position. Optionally, the switching sleeve may be configured with a slot at a second end configured to releasably receive the coupling mechanism and couple the outer sleeve to the switching sleeve. In one embodiment, the apparatus includes a locking mechanism disposed between the pair of distractors to maintain the distractors in their insertion position. In another embodiment, the passage of the apparatus is configured to allow bilateral implantation of a pair of spinal implants into the disc space. In one form, the passage of the outer sleeve includes a first portion and a second portion, the first portion defining a first center and the second portion defining a second center, the first center spaced a distance d from the second center. In another form, the first portion defines a first circular area having a radius R1 and the second portion defines a second circular area having a radius R2. In still a further form, the first circular portion overlaps the second circular portion.

In yet another aspect of the present invention, an apparatus for distracting a disc space and allowing insertion of spinal implants therethrough is provided. The apparatus includes a sleeve having a first end and an opposite second end and a pair of opposite fingers extending from the first end. The sleeve defines a single channel therethrough. The channel includes a first portion and an adjacent second portion each configured to receive a spinal implant for bilateral insertion into the disc space. A sealing member sealingly engages the sleeve at the second end and has at least one bore for sealingly receiving surgical instruments therethrough. The at least one bore is substantially aligned with a corresponding one of the implant insertion portions.

In another aspect of the present invention, a method for preparing a disc space of a patient for implantation of a device between adjacent vertebrae is provided. The method includes the steps of gaining access to the disc space; providing a sleeve assembly including an outer sleeve having a first end and an opposite second end, the outer sleeve defining a passage between the first end and the second end, a switching sleeve disposed within the passage and coupled to the outer sleeve at a second end, the switching sleeve having a locking channel between a pair of opposite distractors extending through the switching sleeve. The sleeve assembly is advanced into the patient until the first end of the sleeve assembly is positioned adjacent the disc space. The sleeve assembly is impacted to insert the distractors into the disc space. Preferably, the distractors are rotatable and are rotated to further distract the disc space. In one more aspect of the method, a guide member is disposed in the disc space and the sleeve assembly is advanced over the guide member to the disc space.

One object of the present invention is to provide surgical techniques and instruments that permit preparation of a disc space for bilateral insertion of a fusion device or vertebral implant with minimal disruption of tissue surrounding the surgical site. A further object of the invention is to enhance the use of laparoscopic techniques with bilateral insertion of vertebral implants.

Other objects and benefits can be discerned from the following written description and the accompanying figures.

DESCRIPTION OF THE PREFERRED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended, any such alterations and further modifications in the illustrated devices, and any such further applications of the principles of the invention as illustrated therein being contemplated as would normally occur to one skilled in the art to which the invention relates.

Figure 1:
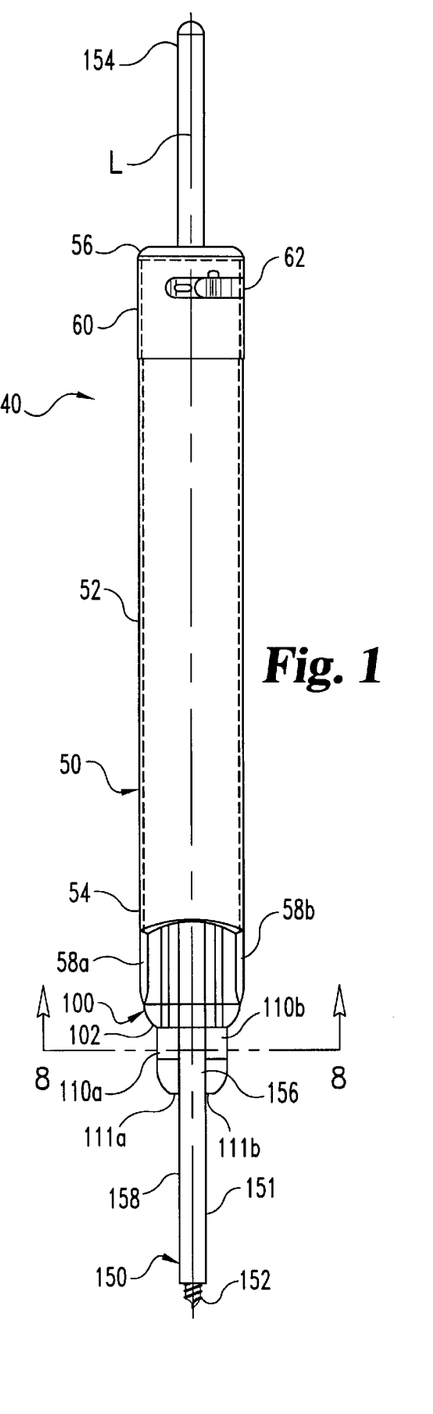
FIG. 1 is an elevational view of surgical instruments comprising one aspect of the present invention.
Figure 2:
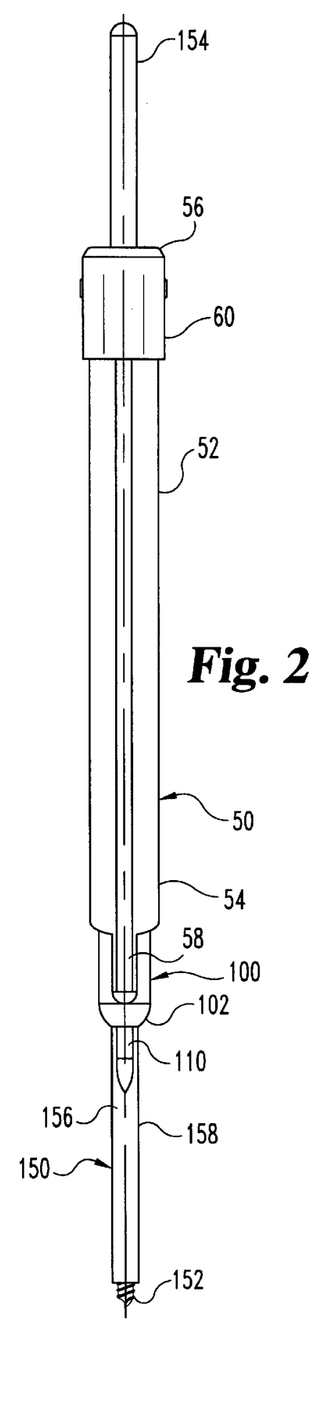
FIG. 2 is a side elevational view of the surgical instruments of FIG. 1.

A preferred embodiment surgical instrument assembly in accordance with the present invention is illustrated in FIGS. 1–2 and designated generally at 40. Assembly 40 includes an outer sleeve 50 with a switching sleeve 100 disposed therethrough. A dilator 150 is disposed through the switching sleeve 100. Surgical instrument assembly 40 is particularly useful for accessing and preparing a disc space for the bilateral insertion of vertebral implants or fusion devices therein. In one aspect of the present invention, the surgical instrument assembly allows surgical procedures to be performed under a relatively sealed and protected passageway in an insufflated environment within the body cavity to prevent the leakage of abdominal distension fluids into the working channel and disc space. This also allows the direct vision of the surgical site outside the working channel created by the outer sleeve 50. The surgical instrument assembly 40 may also find application in fields outside the field of spinal surgery.

Figure 3:
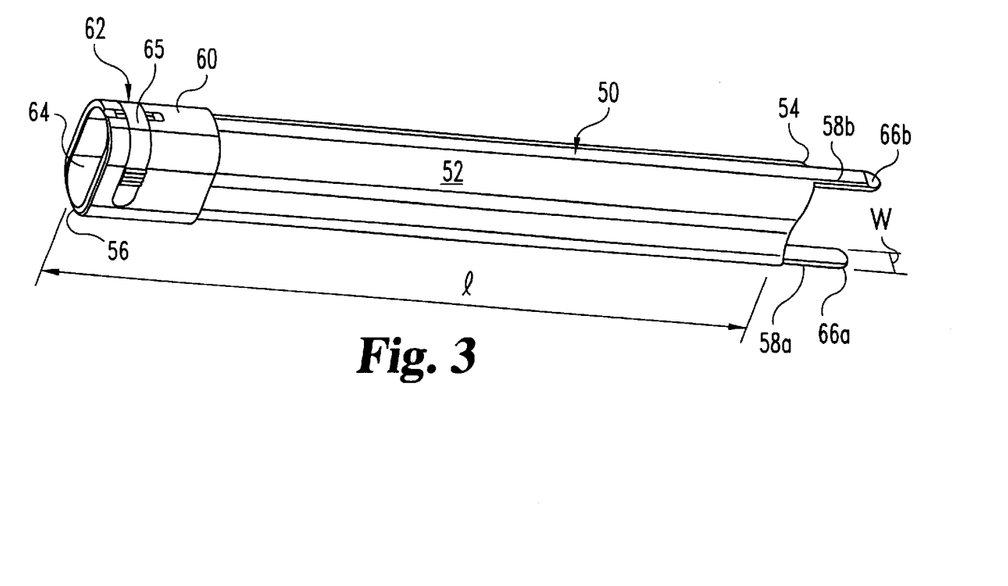
FIG. 3 is a perspective view of the outer sleeve comprising a portion of the surgical instruments of FIG. 1.
Figure 4:
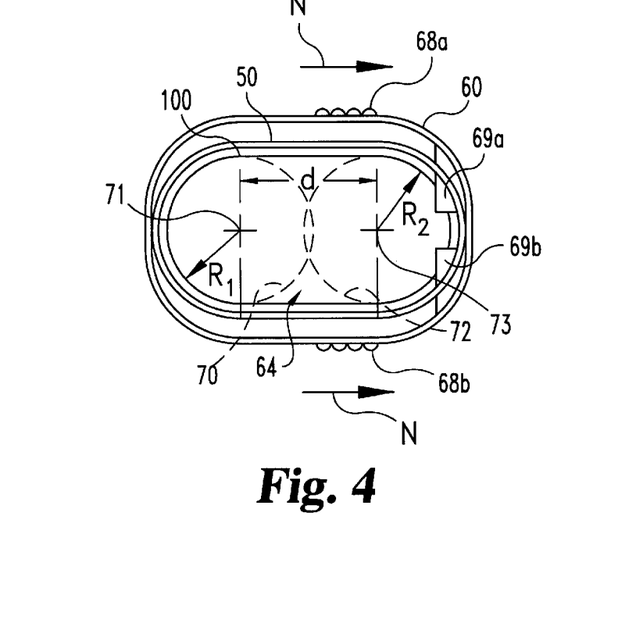
FIG. 4 is a left-hand end view of the outer sleeve of FIG. 3.

Referring additionally to FIGS 3–4, outer sleeve 50 has a first end 54, a second end 56 and a body portion 52 extending therebetween. Body portion 52 defines a passage 64 therethrough extending between first end 54 and second end 56 for receiving, for example, switching sleeve 100 and dilator 150. As described more fully below, passage 64 of outer sleeve 50 is also configured to receive various tools and surgical instruments therethrough in order to perform surgical procedures on the spine. Body portion 52 has a length "l" sufficient to extend from the spine through the skin of the patient in order to allow the surgeon access to the spine through second end 56.

In a further aspect of the outer sleeve 50, first end 54 includes a pair of opposite distraction extensions or fingers 58a and 58b, collectively designated as fingers 58, extending from body portion 52. These fingers 58 are sized according to the desired height of the particular disc space and the depth of the disc space into which the outer sleeve 50 is to be inserted. Specifically, the fingers 58 are intended to maintain the spacing between the adjacent vertebrae during surgical procedures, which procedures will be described more fully below. Thus, the width "W" of the fingers 58 can be varied depending upon the particular vertebral level being instrumented. In addition, fingers 58 can be tapered along their length in order to conform to a normal angle between adjacent vertebrae at the instrumented level. In one embodiment, the fingers 58a and 58b include tapered tips 66a and 66b, respectively, which facilitate insertion into the disc space.

Figure 10:
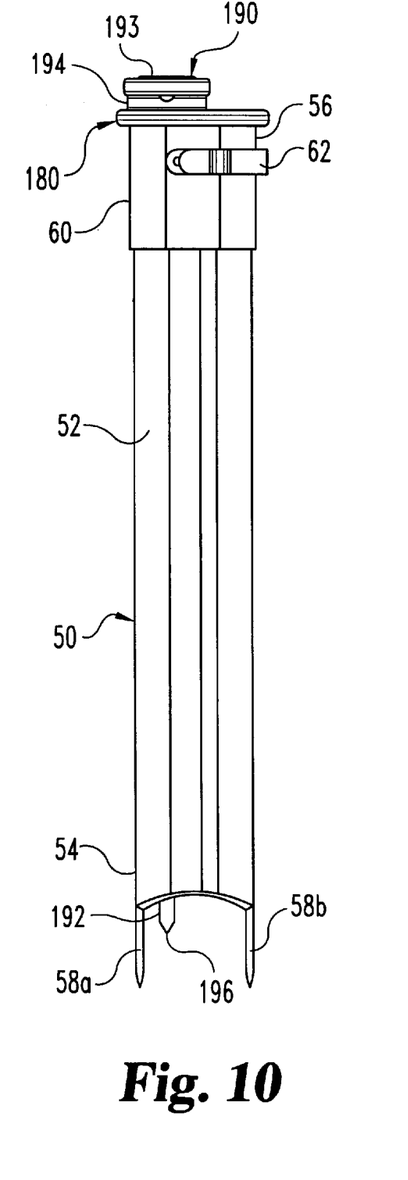
FIG. 10 is an elevational view of the outer sleeve of the present invention with a reaming sleeve disposed therein.

Also provided at second end 56 of outer sleeve 50 is impactor cap 60 which allows an impactor or driving mechanism (not shown) to be used to drive switching sleeve 100 and outer sleeve 50 into the disc space. As shown in FIGS. 3–4, impactor cap 60 includes a coupling mechanism 62 that has a band 65 having opposite ends each engaged to a respective one of a pair of gripping portion 68a and 68b disposed on opposite sides of outer sleeve 50. Band 65 also includes a pair of adjacent inwardly extending tabs 69a and 69b sized and configured to extend through appropriate slots (not shown) in body portion 52 of outer sleeve 50 and through a slot 120 of switching sleeve 100 (see FIGS. 5–5a). The gripping portions 68a and 68b are operable to retract tabs 69a and 69b for insertion of switching sleeve 100 within outer sleeve 50. This is accomplished by gripping the portions 68a and 68b and moving them in the direction of the arrows N. As best seen in FIG. 10, the band 65 may be translated with respect to the impactor cap 60 for this purpose. Gripping portions 68a and 68b are also operable to extend the tabs 69a and 69b, as shown in FIG. 4, to couple or engage switching sleeve 100 to outer sleeve 50. It is also contemplated by the present invention that band 65 be provided with only one tab 69 or more than two tabs 69.

In accordance with one embodiment of the present invention, outer sleeve 50 is provided with passage 64 defining a cross-section having a configuration as shown in FIG. 4. Passage 64 is configured to allow bilateral insertion of implants or devices therethrough into the disc space after outer sleeve 50 is inserted into the disc space. Passage 64 has a first portion 70 and a second portion 72. First portion 70 defines a circle with a radius R1 about a center 71, and second portion 72 defines a circle with a radius R2 about a center 73. In one embodiment, first portion 70 and second portion 72 overlap as shown in FIG. 4. In another embodiment, first portion 70 and second portion 72 do not overlap. Preferably, radii R1 and R2 are equal; however, alternate embodiments contemplate radii for R1 and R2 that are not equal. In one embodiment of the invention, R1 and R2 are about 9 millimeters, and the distance "d" between centers 71 and 73 is about 17 millimeters. However, alternate embodiments contemplate other lengths for radii R1 and R2 and separation distance "d" depending on the requirements of the surgical procedure, the shape and size of the vertebral implants, and the shape and size of the disc space.

Surgical instrument assembly 40 is illustrated with outer sleeve 50, a switching sleeve 100 disposed within outer sleeve 50 and a dilator 150 disposed through switching sleeve 100. Although a dilator is shown as a guide member, in a preferred embodiment any guide member may be used to guide the sleeve assembly to the disc space. Dilator 150 has a first end portion 151, a second end portion 154, and a stem 156 extending therebetween. Second end portion 154 serves as a handle that projects from outer sleeve 50 to allow dilator 150 to be moved by the surgeon with respect to switching sleeve 100 and outer sleeve 50. First end 151 is threaded to receive any one of a number of various-sized detachable dilator tips (not shown) used for insertion into the disc space. An appropriate-sized dilator tip is selected according to the vertebral level being instrumented. While not required, progressively larger dilator tips may be sequentially inserted in alternating fashion into the disc space through the annulus of the disc until the annulus and the adjacent vertebrae are adequately dilated.

Figure 5:
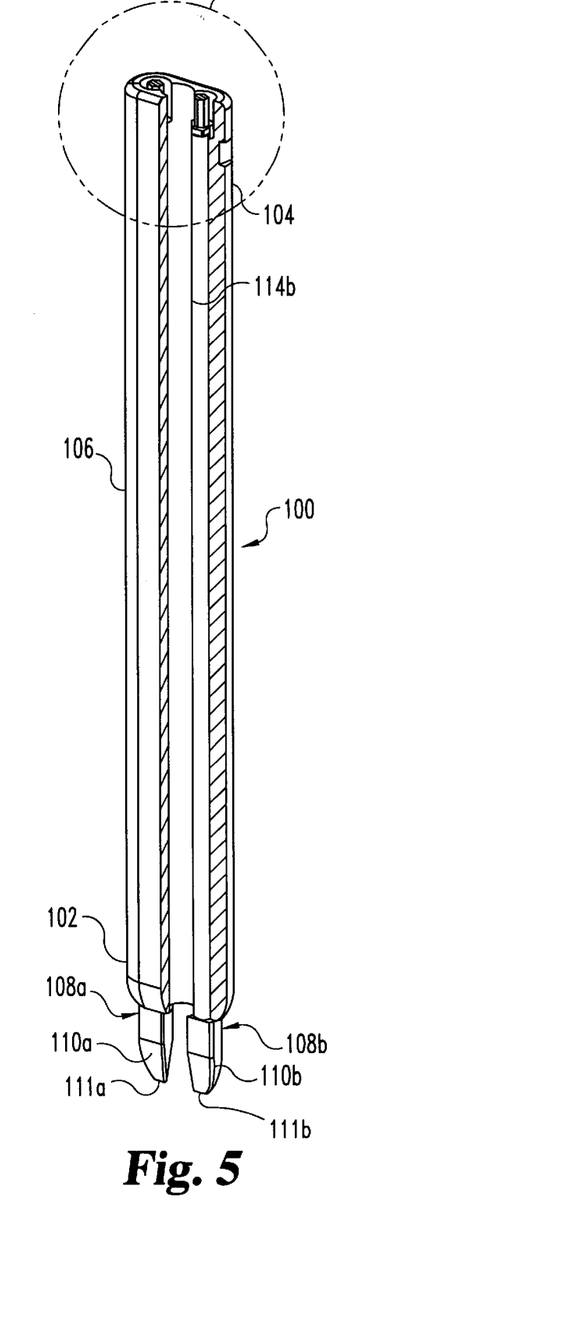
FIG. 5 is a partially fragmented perspective view of a switching sleeve comprising another portion of the surgical instruments of FIG. 1.
Figure 5A:
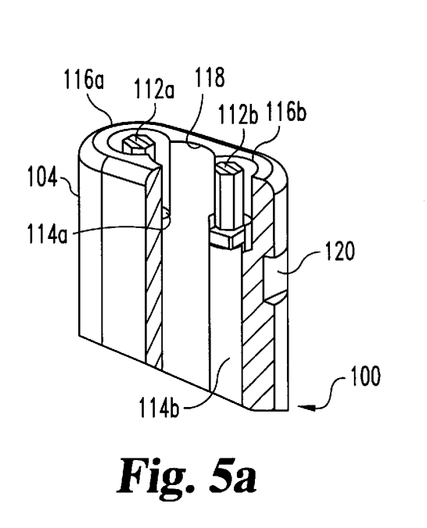
FIG. 5a is an enlarged perspective view of a portion of the sleeve of FIG. 5.

Switching sleeve 100 is illustrated and will now be described with reference to FIGS. 5–5a. Switching sleeve 100 has a first rounded end 102 and a second end 104 with a body portion 106 extending therebetween. Rounded end 102 is configured to ease insertion of the assembly through the tissue as it is advanced to the disc space. Body portion 106 is sized and configured to be slidingly received within outer sleeve 50 in close fitting relation. Switching sleeve 100 also includes distractors 108a and 108b releasably engaged in the switching sleeve and operable to distract a disc space. Distractors 108a and 108b each include a distractor head 110a and 110b extending from the second end 102 of switching sleeve 100. Distractor heads 110a and 110b are engaged to and extend from a corresponding shaft 114a and 114b. Body portion 106 defines slot 120 proximate second end 104 to receive tabs 69a and 69b of coupling mechanism 62 in order to engage outer sleeve 50 to switching sleeve 100. Body portion 106 further defines a pair of distractor channels 116a and 116b extending between first end 102 and second end 104. A locking channel 118 is also defined by body portion 106 and extends from first end 102 to second end 104 between distractor channels 116a and 116b (see also FIGS. 8–9). Distractor channels 116a and 116b are each sized to rotatably receive a respective distractor shaft 114a and 114b therethrough. Distractor shafts 114a and 114b extend from engagement portions 112a and 112b adjacent second end 104 to distractor heads 110a and 110b adjacent first end 102.

In order to manipulate the heads 110a and 110b through the body portion 106 of switching sleeve 100, engagement portions 112a and 112b are provided on shafts 114a and 114b proximate second end 104 of sleeve 100. In a preferred embodiment, engagement portions 112a and 112b are nuts for placement of a socket-type mechanism thereover. However, other embodiments contemplate other structures for engagement portions 112a and 112b including, for example, a receptacle for a drive mechanism, or any other mechanism such as would occur to those skilled in the art. Each of the distractor heads 110a and 110b includes a tip 111a and 111b to facilitate insertion of the distractor heads 110a and 110b into disc space after dilation by dilator 150. Preferably, tips 111a and 111b are tapered to enlarge from a relatively thin tip at the distal end of the distractor heads 110a and 110b towards the shafts 114a and 114b. Each of the distractor heads 110a and 110b define an inward face 115a and 115b, respectively, configured to engage the stem 156 of dilator 150 when stem 156 is disposed between surfaces 115a and 115b. Preferably, surfaces 115a and 115b are curved inwardly with respect to distractor heads 110a and 110b in order to provide a form fitting engagement with stem 156.

Switching sleeve 100 and outer sleeve 50 are lockingly coupled prior to insertion over dilator 150 and through the skin to the disc space. Impactor cap 60 with coupling mechanism 62 is positioned about second end 56 of outer sleeve 50. Outer sleeve 50 is then slid over switching sleeve 100 and coupled thereto by manipulating gripping portions 68a and 68b until tabs 69a and 69b extend through slot 120 of switching sleeve 100. In order to unlock the sleeves 50 and 100, gripping portions 68a and 68b are slid in the direction indicated by arrow N to displace band 65 and tabs 69a and 69b from the slot 120. When coupling mechanism 62 is in the unlocked position, outer sleeve 50 and switching sleeve 100 slide with respect to one another. When coupling mechanism 62 is in the locked position, outer sleeve 50 and switching sleeve 100 move in conjunction with one another.

Figures 6, 6A:
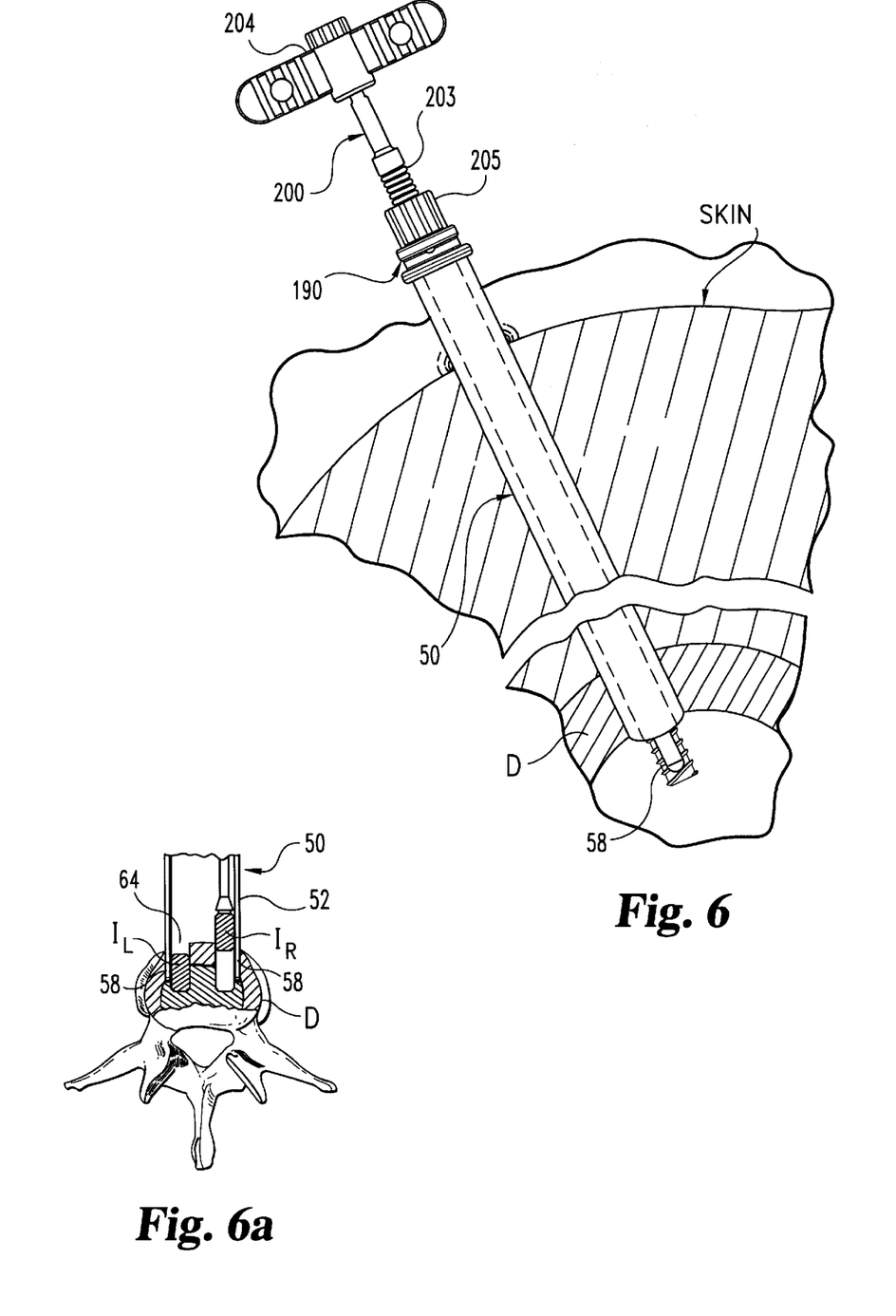
FIG. 6 is a perspective representation of the surgical instruments of the present invention comprising an outer sleeve engaged in a disc space and an implant insertion device disposed within the outer sleeve.
FIG. 6a is an enlarged anterior-posterior representation of a portion of the surgical instruments of FIG. 6 showing bilateral positioning of implants within the disc space.

In accordance with a preferred embodiment of an inventive surgical procedure, the placement of outer sleeve 50 within the patient as shown in FIGS. 6–6a will now be described. Preferably, the surgical procedure described herein is performed via an anterior approach to the spine. However, the surgical instruments of the present invention are not limited to such an approach, and may find application in posterior and latero-posterior approaches as well. Additionally, the surgical instruments of the present invention may find application at all vertebral segments of the spine, and in areas other than spinal surgery.

FIG. 6a illustrates outer sleeve 50 with distraction finger 58a inserted into a disc space D. The configuration of outer sleeve 50 allows surgical procedures to be performed within the disc space D in order to, for example, prepare the disc space and insert vertebral implants at left bilateral location $I_L$ and a right bilateral location $I_R$. It should be appreciated that the design and configuration of outer sleeve 50 allows the procedures to be performed in the disc space D at locations $I_L$ and $I_R$ through a single working channel or passage 64.

In order to insert the outer sleeve 50 into disc space D as shown in FIGS. 6–6a, it is necessary to properly position the patient and prepare the surgical site for an anterior approach to the spine. Techniques for preparing the surgical site for entry by a working trocar and dilator are known to those skilled in the art. One such technique is disclosed in PCT Publication No. WO 97/30666, which is incorporated herein by reference. However, it should be understood that the present invention does not require the use of bi-portal entries through the abdomen of the patient or manipulation of outer sleeve 50 through the skin after initial placement in order to insert bilateral vertebral implants or fusion devices within the disc space.

In order for the dilator tip 152 to be positioned within the disc space, it is first necessary to retract the tissue between the skin level and the subject disc space by insertion of a working trocar (not shown) through an incision made in the skin of the patient. The insertion and placement of a working trocar to the spine via an anterior approach is well-known in the art, and will not be described in detail herein. Once the working trocar is positioned, the dilator 150 is inserted through the trocar with the appropriate sized tip 152 into the disc space. Dilator 150 then acts as a centering or guiding member for use with switching sleeve 100 and outer sleeve 50 throughout the procedure. It is therefore important that dilator 150 be properly located within the disc space, which can be accurately confirmed with fluoroscopy.

After the dilator tip 152 and dilator 150 are inserted through the trocar and into the disc space, the working trocar may be removed. The switching sleeve 100 and outer sleeve 50 may be installed over stem portion 156 of dilator 150. It may first be necessary to slightly enlarge the incision created through the skin for the working trocar to allow placement of the switching sleeve 100 and outer sleeve 50 through the skin. Switching sleeve 100 is placed within outer sleeve 50 and engaged via coupling mechanism 62 as described above. As shown in FIGS. 1–2, distractors 108a and 108b extend beyond the fingers 58a and 58b when sleeves 50 and 100 are assembled. The assembly of sleeves 50 and 100 is then slidingly advanced over stem 156 of dilator 150 through the enlarged incision in the skin. It may be necessary for the surgeon to slightly twist or wrest the sleeve assembly of 50 and 100 about the stem 156 in order to advance the assembly through the skin to the disc space D.

Figure 8:
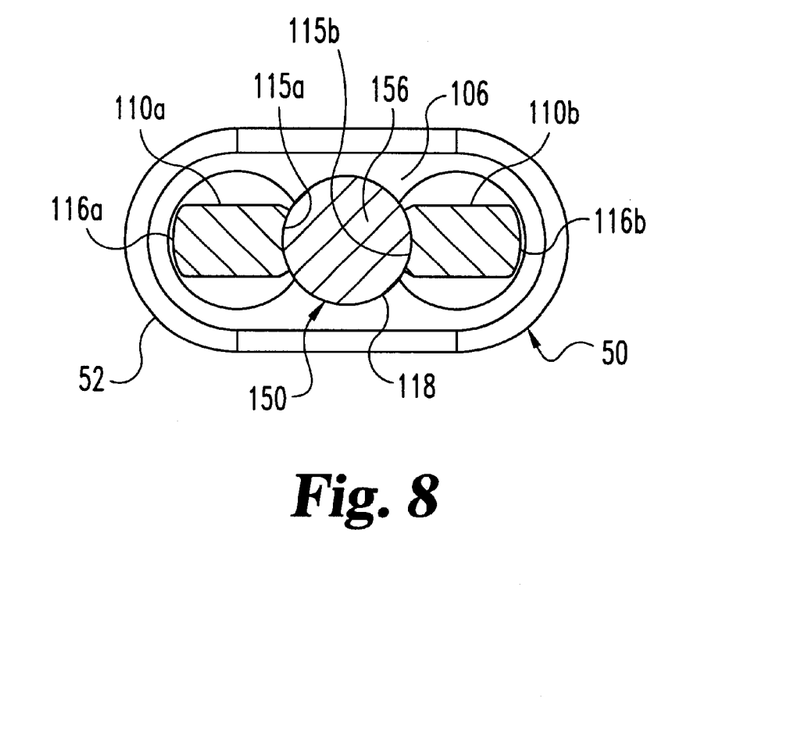
FIG. 8 is a cross-sectional view taken along line 8—8 of FIG. 1.

The switching sleeve 100 and outer sleeve 50 are advanced over dilator 150 until tips 111a and 111b of distractors 108a and 108b are positioned adjacent the annulus. The distractors 108a and 108b are placed in an insertion position such that the wide axis of each of the tips 111a and 111b runs perpendicular to longitudinal axis L extending through outer sleeve 50. The sleeve assembly 50 and 100 is advanced over the dilator 150 in a manner such that tips 111a and 111b runs parallel to the disc space D (perpendicular to the axis formed by the spinal column). The dilator 150 is received within locking channel 118, as shown in FIG. 8, as the sleeves 50 and 100 are advanced thereover and locks distractor heads 110a and 110b to their insertion position. Thus, dilator 150 serves as a locking mechanism and prevents the distractor heads 110a and 110b from rotating and becoming misaligned in the disc space D during the insertion of sleeves 50 and 100. In order to place the distractor heads 110a and 110b into the disc space, longitudinal force is applied to the impactor cap 60 in order used to impact switching sleeve 100 through outer sleeve 50 until the heads 110a and 110b are in the desired location within the disc space D.

Figure 7:
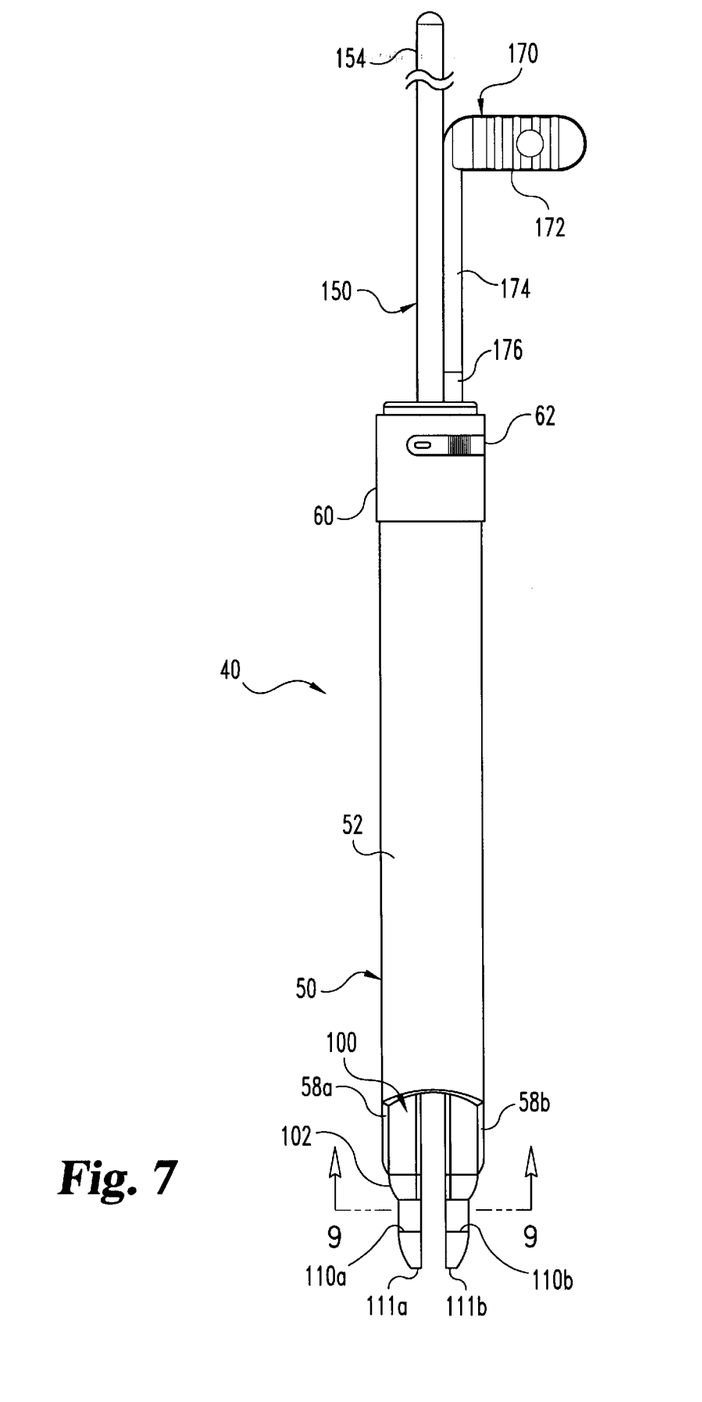
FIG. 7 is an elevational view of the surgical instruments of the present invention with a distracter handle engaged thereto.

Referring now to FIG. 7, if greater distraction is desired, the distractors may be rotated to a greater height. In order to rotate the distractor heads 110a and 110b within the disc space, a distractor handle 170 is placed on and engaged with a respective one of the engagement portions 112a and 112b. Although shown in FIG. 7 with only one distractor handle 170, it is contemplated herein that a separate distractor handle 170 may be provided on each engagement portion 112a and 112b in order to simultaneously rotate distractor heads 110a and 110b to distract the disc space D. While not required, simultaneous distraction may limit the potential for vertebral or instrument displacement as a result of unilateral disctraction. Preferably, distractor handle 170 includes a gripping portion 172 and a stem 174 extending to a coupling portion 176. Coupling portion 176 is configured to engage engagement portions 112a and 112b to rotate the distractors 108a and 108b upon rotation of the gripping portions 172.

Figure 9:
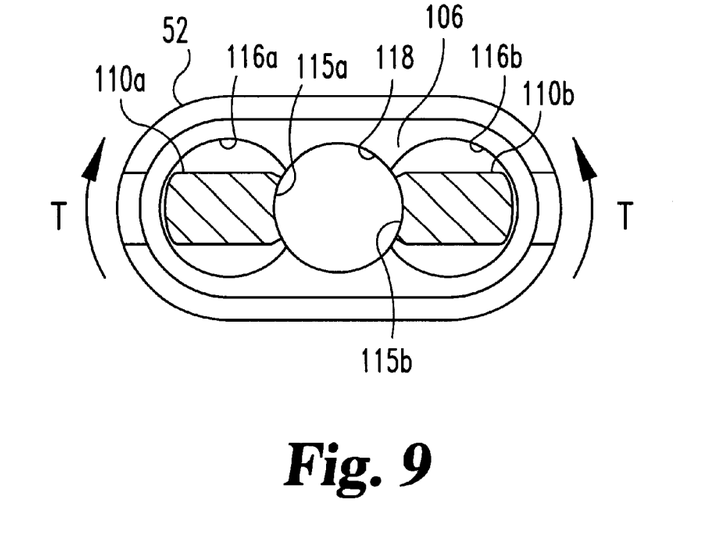
FIG. 9 is a cross-sectional view taken along line 9—9 of FIG. 7.

Referring additionally to FIGS. 8–9, in order to release distractor heads 110a and 110b for rotation, the dilator 150 is pulled within locking channel 118 of switching sleeve 100 until stem 156 is no longer engaged by surfaces 115a and 115b of the distractor heads 110a and 110b. Preferably, dilator 150 is only partially withdrawn into switching sleeve 150 to release distractor heads 110a and 110b for rotation. In another embodiment, the dilator 150 must be fully withdrawn from switching sleeve 100 in order to release distractor heads 110a and 110b for rotation. Once the distractor heads 110a and 110b are released for rotation, the distractor handle(s) 170 are then rotated by the surgeon in order distract the disc space D with the distractor heads 110a and 110b. Preferably, the disc space is distracted evenly by simultaneously rotating the distractor heads 110a and 110b. Alternate embodiments contemplate that the disc space D is distracted by sequentially rotating the distractor heads 110a and 110b. It is also contemplated that rotation of distractor heads 110a and 110b may be accomplished by rotating each distracter 108a and 108b in the same direction or in opposite directions with distractor handle 170.

Referring now to FIGS. 8–9, the cross-sections of switching sleeve 100 with distractors 108a and 108b locked and unlocked are illustrated. In FIG. 8, distractors 108a and 108b are locked by the extension of dilator 150 therebetween. In this position, the distractors 108a and 108b may be inserted into the disc space. It should be noted that outer sleeve 150 is disposed around and engaged to switching sleeve 100 via coupling mechanism 62 as described above during insertion of distractors 108a and 108b into the disc space. In order to rotate distractors 108a and 108b, dilator 150 is pulled out of the disc space until it is in a position such as that shown in FIG. 7. When the dilator 150 is in this position, heads 110a and 110b may be rotated in, for example, the directions indicated by arrows T of FIG. 9 in order to distract the disc space. Once the distractors 108a and 108b are completely rotated, the tips 111a and 111b extend parallel to the axis of the spinal column.

When switching sleeve 100 is inserted into the disc space, and the distractors 108a and 108b are rotated to fully distract the disc space to the desired height, fingers 58a and 58b of outer sleeve 50 may be inserted into the disc space. First, locking mechanism 62 is manipulated to uncouple outer sleeve 50 from the switching sleeve 100. The outer sleeve 50 may be seated by striking impactor cap 60 mounted on second end 54 to drive the fingers 58a and 58b fully into the disc space between the vertebral end plates to the desired depth. As the fingers 58a and 58b are pushed into the disc space, the heads 110a and 110b of distractors 108a and 108b remain inside the disc space in their seated position in the region between fingers 58a and 58b.

Once fingers 58a and 58b are fully inserted and seated into the disc space D, switching sleeve 100 may be removed from the passage 64 of outer sleeve 50. The distractors 108a and 108b are rotated to their insertion position, and the switching sleeve 100 is withdrawn (along with dilator 150, if necessary) from the outer sleeve 50. In one embodiment, at least one spike (not shown) is provided between the distractor fingers 58a and 58b extending from body portion 52 in order to engage the adjacent vertebrae. The spikes are driven into the vertebrae as the fingers are driven into the disc space.

Figure 10A:
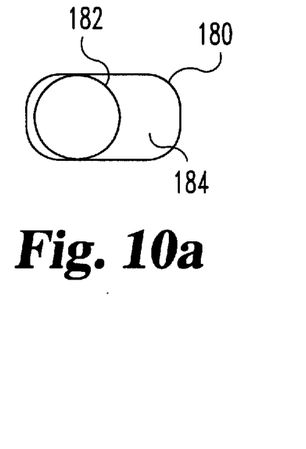
FIG. 10a is a seal according to one aspect of the present invention.

In one embodiment of the present invention, the switching sleeve 100 is removed and the outer sleeve 50 is in place, all the remaining steps of the present surgical technique may occur under a relatively protected or sealed environment. Specifically, the outer sleeve 50 of the surgical instrument apparatus may be provided with a sealing member 180 (see FIG. 10a). Sealing member 180 seals a portion of passage 64 and the disc space D from the environment outside the patient, which allows maintenance of the insufflation pressure in the abdomen of the patient during laparoscopic procedures. The sealing member 180 has a port 182 to permit passage of instruments therethrough and a body portion 184 to sealingly engage and allow passage of surgical instruments therethrough without loss of insufflation pressure. Sealing member 80 is preferably made of stainless steel and relies on the close tolerances between instruments disposed therein and the diameter of the port to maintain the seal. Thus, when outer sleeve 50 is sealed via sealing member 180, as shown in FIG. 10, a portion of channel 64 may be used as a passageway to provide irrigation and aspiration, when necessary, without the risk of fluids leaking into the space adjacent the operative site. Moreover, the sealed working channel extending to the prepared sites and the disc space prevents leakage of abdominal distention fluids into the working channel and disc space. This latter aspect allows direct vision of the surgical site outside the working channel created by the outer sleeve 50 through a laparoscopic port. While sealing member 180 is shown with a single port, it is contemplated that more than one port may be provided along with covers to seal unused ports.

With the distractors 108a and 108b removed from the disc space and the disc space supported by fingers 58a and 58b, the next step of the present method is to prepare the vertebral end plates and disc space for insertion of, for example, a fusion device or vertebral implant. The instruments and techniques used to prepare the disc space D for insertion of vertebral devices or implants will now be described with reference to FIGS. 10–12. In FIG. 10, a reaming sleeve 190 is advanced through port 182 of sealing member 180 into first portion 70 or alternately, second portion 72 of passage 64 of outer sleeve 50. Reaming sleeve 190 has a first end 192 with a pair of spikes 196 for engaging the adjacent vertebral bodies to hold the reaming sleeve 190 in place. Reaming sleeve 190 also has a second end 194 with an entry port 198 defined thereby and having diameter substantially equal to the diameter of port 182.

Figure 11:
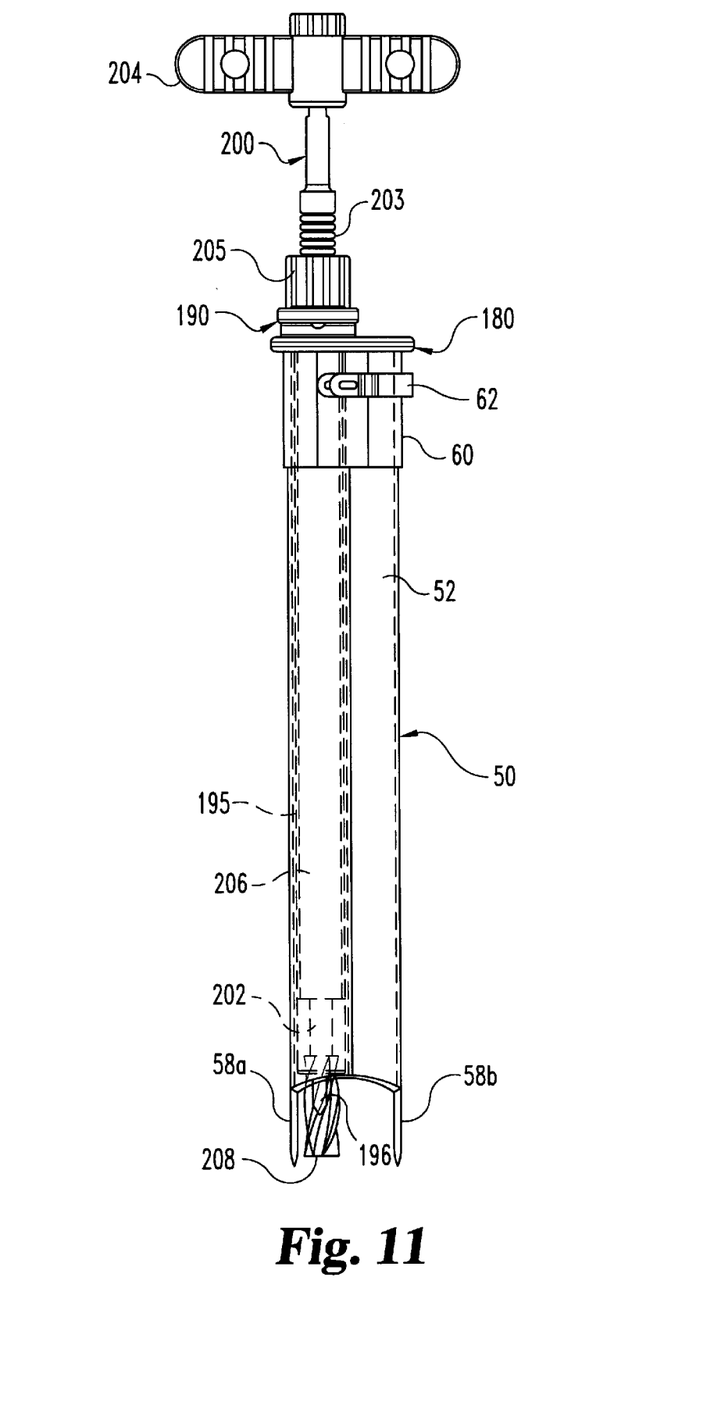
FIG. 11 is an elevational view of the outer sleeve of FIG. 10 with a reamer disposed through the sleeve.

The reaming sleeve is sized to receive the reamer 200 through entry port 198 to ream the disc space and prepare the vertebral endplates for an implant or fusion device. The reamer 200 is of a conventional design with a cutting member 208 at first end 202 configured to evacuate the disc space and prepare adjacent vertebral bodies to receive an implant or fusion device. A second end 203 has an adjustable stop 205 to prevent introduction of the reamer 208 too deeply into the disc space. The depth of reaming necessary, and consequently the position of the depth stop 205, can be determined prior to the reaming step by review of fluoroscopic images.

The reamer 200 is manually operated by way of a T-handle 204 positioned adjacent second end 203. The T-handle 204 allows manual operation of the cutting member 208 to successively remove disc tissue and bone from adjacent vertebral bodies to provide a prepared bore for the fusion implant or vertebral spacer device. In FIGS. 10–11, the reaming sleeve 190 and reamer 200 are positioned within first portion 70 of passage 64 of outer sleeve 50 to prepare the left lateral location $I_L$ of the disc space. Once the $I_L$ site is prepared, the reamer 200 may be repositioned along with the reaming sleeve 190 in the second passage 72 to prepare the right lateral location $I_R$ to receive a vertebral spacer or fusion device.

Figure 12:
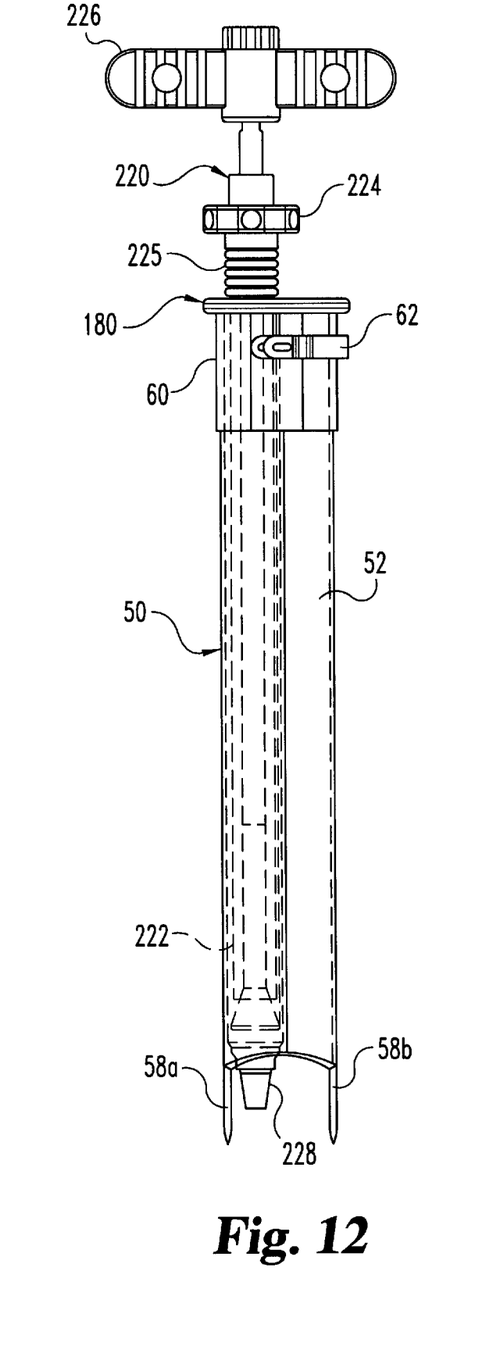
FIG. 12 is an elevational view of the outer sleeve of the present invention with an implant insertion device disposed therethrough.

Once each of the bilateral sites for implantation of the vertebral devices have been prepared, the reamer 200 and reaming sleeve 190 may be withdrawn from passage 64 of the outer sleeve 50. In order to insert the implants, an implant insertion device 220 is provided as shown in FIG. 12. Implant insertion device 220 likewise extends through passage 64 of outer sleeve 50 in order to place an implant at the desired left or right lateral location $I_L$ and $I_R$ within the disc space. Implant insertion device 220 has a first end 222 configured to engage an implant during insertion. Implant insertion device 220 has a second end 224 with handle 226 to allow the surgeon to thread or impact the implant to the desired depth in the $I_L$ and $I_R$ locations. Second end 224 also includes depth markings 225 to allow the surgeon to determine the depth of insertion of the implant. It is contemplated herein that first end 222 has a grasping portion 228 for holding the implant as it is being inserted. In one embodiment, grasping portion 228 includes a pair of arms biased against sidewalls of the implant that allow the implant to be threaded or impacted into the disc space. Once the implant is inserted into one of the bilateral locations $I_L$ or $I_R$, the implant insertion tool 220 may be removed from outer sleeve 50. A second implant is engaged to insertion tool 220 and reinserted through passage 64 of outer sleeve 50 to insert the implant at the other bilateral location after it is prepared.

It should be appreciated that the bilateral sites $I_L$ and $I_R$ may be prepared without movement or manipulation of outer sleeve 50 through the skin of the patient after the fingers 58a and 58b are positioned within the disc space. Moreover, once sleeve 50 has been placed, there is a requirement for further manipulation of tissue adjacent the vertebral bodies. The surgeon has access to each of the locations $I_L$ and $I_R$ through the single channel defined by the outer sleeve 50. It should be further appreciated that the entire disc space between fingers 58a and 58b may be reamed or otherwise prepared for insertion of a vertebral implant, spacer device, or bone growth material without movement of outer sleeve 50. It is contemplated herein that the outer sleeve 50 may be used for preparation and insertion of a single implant or device, or two or more implants or devices, depending upon the needs of the patient.

The present invention is advantageous over prior surgical techniques. It allows preparation of bilateral locations for implants to be accurately located and maintained throughout the duration of the surgical procedure. Another advantage to the present invention is that it allows preparation of the disc space and insertion of the implants into the disc space under direct observation via laparoscopic techniques. While it is preferable that the implants and devices inserted through the outer sleeve be cylindrical, this configuration is not essential to the invention, provided the implant or devices are configured to pass through the outer sleeve 50. Specifically, while other geometries are contemplated, outer sleeve may have a substantially square or rectangular cross-section for placement of similarly spaced implants. The present invention also allows the positioning of the implants to be verified and adjusted easily without movement or removal of outer sleeve 50 or disruption of the sealed passageway between the disc space and the environment outside the patient's body.

While the invention has been illustrated and described in detail in the drawings and foregoing description, the same is to be considered as illustrative and not restrictive in character, it being understood that only the preferred embodiments has been shown and described and that all changes and modifications the come within the spirit of the invention are desired to be protected.

What is claimed is:

1. A method for preparing a disc space of a patient for implantation of a device between adjacent vertebrae comprising the steps of:
    a) gaining access to the disc space;
    b) providing a sleeve assembly including an outer sleeve having opposite fingers extending from a first end and an opposite second end, the outer sleeve defining a passage between the first end and the second end, a switching sleeve disposed within the passage and coupled to the outer sleeve at a second end, the switching sleeve having a locking channel between a pair of opposite rotatable distractors extending through the switching sleeve;
    c) advancing the locking channel of the sleeve assembly over the dilator until the first end of the sleeve assembly is positioned adjacent the disc space; and
    d) impacting the sleeve assembly to insert the distractors into the disc space to distract the disc space.

2. The method according to claim 1, further comprising the steps of:
    e) uncoupling the switching sleeve from the outer sleeve; and
    f) impacting the outer sleeve to drive the opposite fingers of the outer sleeve into the disc space.

3. The method of claim 2, further comprising the steps of:
    g) withdrawing the switching sleeve from the outer sleeve; and
    h) placing a sealing member for protecting the passage of the outer channel, the sealing member having at least one bore therethrough for sealingly receiving surgical instruments therethrough.

4. The method of claim 3, further comprising the steps of:
    i) inserting a reaming sleeve through the at least one bore of the sealing member;
    j) inserting a reamer through the reaming sleeve; and
    k) reaming a first location in the disc space with the reamer.

5. The method of claim 4, further comprising the steps of:
    l) withdrawing the reamer and reaming sleeve from the outer sleeve; and
    m) inserting an implant insertion device through the seal; and
    n) inserting an implant into the disc space.

6. The method of claim 5, wherein steps (l) through (n) are repeated for insertion of a second implant at a second location in the disc space bilateral of the first location.

7. The method according to claim 1, wherein step (a) further includes placing a trocar through the incision to retract the tissue and expose the disc space.

8. The method according to claim 1, further including after step (a), inserting a guiding member into the disc space and wherein step (c) includes advancing over the guide member.

9. The method according to claim 1, wherein the pair of distractors are rotatable and further including after step (d), rotating the distractor to further distract the disc space.

10. An apparatus for distracting a dilated disc space, comprising:
    a switching sleeve having a first end and an opposite second end, said sleeve defining a pair of distractor channels and a locking channel between said pair of distractor channels, said distractor and locking channels extending between said first and second ends; and
    a pair of distractors rotatably received within a corresponding one of said distractor channels, each of said distractors having a head extending from said first end, an engagement portion proximate said second end, and a stem extending between said head and said engagement portion,
    wherein said locking channel is configured to receive a locking mechanism for locking said heads in an insertion position for insertion into the dilated disc space, said locking mechanism being movable after said heads are inserted into the disc space to release said heads for rotation to a second position to distract said disc space.

11. The apparatus of claim 10, wherein said head of said distractors defines a tip, said body being tapered to said head.

12. The apparatus of claim 10, wherein said engagement portion is configured for removably receiving a handle operable to rotate a corresponding one of the distractors.

13. The apparatus of claim 10, wherein said locking channel defines a circular cross-section.

14. The apparatus of claim 10, further comprising a locking mechanism slidably received within said locking channel, said locking mechanism slidable from a locking position wherein said distractors are locked in said first position to a release position wherein said distractors are rotatable to said second position.

15. The apparatus of claim 14, wherein said locking mechanism is a stem of a dilator.

16. An apparatus for use in preparing a disc space for insertion of a vertebral implant, comprising:
    an outer sleeve having a first end with a pair of opposite fingers extending therefrom and an opposite second end having a coupling mechanism, said outer sleeve defining a passage therethrough extending between said first end and said second end; and
    a switching sleeve removably disposed within said passage, said switching sleeve having a pair of distractors at a first end rotatable from an insertion position to a distraction position and a slot at a second end, said slot configured to releasably receive said coupling mechanism to couple said outer sleeve to said switching sleeve.

17. The apparatus of claim 16, further comprising a locking mechanism disposed between said pair of distractors to maintain said distractors in said insertion position.

18. The apparatus of claim 17, wherein said locking mechanism is a stem of a dilator.

19. The apparatus of claim 16, wherein said passage is configured to allow bilateral implantation of a pair of spinal implants into the disc space.

20. The apparatus of claim 16, wherein said passage of said outer sleeve includes a first portion and a second portion, said first portion defining a first center and said second portion defining a second center, said first center spaced a distance d from said second center.

21. The apparatus of claim 20, wherein said first portion defines a circular area having a radius R1 and said second portion defines a circular area having a radius R2.

22. The apparatus of claim 21, wherein R1 is equal to R2.

23. The apparatus of claim 16, wherein said coupling mechanism includes a band extending between a pair of gripping portions oppositely opposed about said outer sleeve, said band including a pair of tabs extending therefrom to extend through said slot to couple said switching sleeve to said outer sleeve when said gripping portions are in a locked position.

24. An apparatus for distracting a disc space and allowing insertion of spinal implants therethrough, said apparatus comprising:

a sleeve having a first end and an opposite second end, said sleeve including a pair of opposite fingers extending from said first end, said sleeve defining a single channel therethrough, said channel including:

a first portion and an adjacent second portion in communication with said first portion, said first and second portions each being sized and positioned with respect to one another to receive one of the spinal implants, so that the spinal implants can be bilaterally positioned in the disc space through a corresponding one of the first and second portions;

a sealing member sealingly engaged to said sleeve at said second end, said sealing member having at least one bore for sealingly receiving surgical instruments therethrough, said at least one bore being substantially alignable with each of said first and second portions.

25. The apparatus of claim 24, wherein said at least one bore is two bores, each of said bores substantially aligned with a corresponding one of said first and second portions.

26. The apparatus of claim 24, wherein said passage has a racetrack shaped cross-section.

27. The apparatus of claim 24, wherein said passage of said outer sleeve includes a first portion and a second portion, said first portion defining a first center and said second portion defining a second center, said first center spaced a distance d from said second center.

28. The apparatus of claim 27, wherein said first portion defines a circular area having a radius R1 and said second portion defines a circular area having a radius R2.

29. The apparatus of claim 27, wherein R1 is equal to R2.

* * * * *